United States Patent [19]

Allais et al.

[11] 4,107,310
[45] * Aug. 15, 1978

[54] QUINOLINE-3-CARBOXAMIDES

[75] Inventors: André Allais, Gagny; Francois Clémence, Rosny-sous-Bois; Roger Deraedt, Pavillons-soùs-Bois; Odile Le Martret, Paris, all of France

[73] Assignee: Roussel Uclaf, Paris, France

[ * ] Notice: The portion of the term of this patent subsequent to Nov. 16, 1993, has been disclaimed.

[21] Appl. No.: 766,487

[22] Filed: Feb. 7, 1977

[30] Foreign Application Priority Data

Feb. 11, 1976 [FR] France ............................ 76 03754

[51] Int. Cl.² .................. A61K 31/47; C07D 215/20
[52] U.S. Cl. ................... 424/258; 260/283 S; 260/287 AN; 260/287 CE; 260/287 F; 260/287 G; 260/295 AM; 260/307 R; 260/562 R; 260/576; 560/9; 560/44; 560/45; 548/316; 548/336
[58] Field of Search ......... 260/287 F, 283 S, 287 CE, 260/287 G, 287 AN; 424/258

[56] References Cited

U.S. PATENT DOCUMENTS 3,197,473  7/1965  Klosa ................................... 260/287
3,992,540  11/1976  Clémence et al. ................... 424/258

Primary Examiner—Donald G. Daus
Assistant Examiner—Lisa Jones
Attorney, Agent, or Firm—Hammond & Littell

[57] ABSTRACT

Novel quinoline-3-carboxamides of the formula

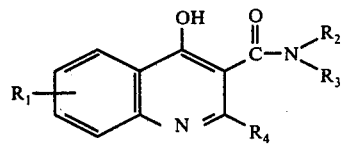

wherein $R_1$ is in the 5,6,7 or 8-position and is selected from the group consisting of hydrogen, halogen, —$CF_3$, —$OCF_3$, —$SCF_3$, straight chain alkyl of 1 to 4 carbon atoms, branched alkyl of 3 to 5 carbon atoms and alkoxy of 1 to 4 carbon atoms, $R_2$ is selected from the group consisting of hydrogen and methyl, $R_3$ is selected from the group consisting of thiazolyl, 4,5-dihydrothiazolyl, pyridinyl, oxazolyl and imidazolyl and $R_4$ is selected from the group consisting of hydrogen, hydroxyl, alkyl of 1 to 4 carbon atoms, phenyl and benzyl with the proviso that when $R_1$ is in the 7 or 8-position and is halogen, —$CH_3$, —$OCF_3$ or —$SCF_3$ and $R_4$ is hydrogen, $R_3$ is not thiazolyl, pyridinyl or oxazolyl and the non-toxic, pharmaceutically acceptable acid addition salts when $R_3$ is imidazolyl or 4,5-dihydrothiazolyl having analgesic activity and their preparation and novel intermediates therefore.

25 Claims, No Drawings

QUINOLINE-3-CARBOXAMIDES

OBJECTS OF THE INVENTION

It is an object of the invention to provide the novel quinoline-3-carboxamides of formula I and a novel process for the preparation of the said compounds and novel intermediates therefor.

It is another object of the invention to provide novel analgesic compositions and a novel method of relieving pain in warm-blooded animals.

These and other objects and advantages of the invention will become obvious from the following detailed description.

THE INVENTION

The novel quinoline-3-carboxamides of the invention have the formula

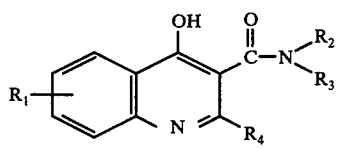

wherein $R_1$ is in the 5,6,7 or 8-position and is selected from the group consisting of hydrogen, halogen, $-CF_3$, $-OCF_3$, $-SCF_3$, straight chain alkyl of 1 to 4 carbon atoms, branched alkyl of 3 to 5 carbon atoms and alkoxy of 1 to 4 carbon atoms, $R_2$ is selected from the group consisting of hydrogen and methyl, $R_3$ is selected from the group consisting of thiazolyl, 4,5-dihydrothiazolyl, pyridinyl, oxazolyl and imidazolyl and $R_4$ is selected from the group consisting of hydrogen, hydroxyl, alkyl of 1 to 4 carbon atoms, phenyl and benzyl with the proviso that when $R_1$ is in the 7 or 8-position and is halogen, $-CF_3$, $-OCF_3$ or $-SCF_3$ and $R_4$ is hydrogen, $R_3$ is not thiazolyl, pyridinyl or oxazolyl and the non-toxic, pharmaceutically acceptable acid addition salts when $R_3$ is imidazolyl or 4,5-dihydrothiazolyl. Among the preferred compounds of formula I are those wherein $R_4$ is hydrogen, hydroxyl or alkyl of 1 to 4 carbon atoms.

Among the compounds of formula I, $R_1$ may be a halogen such as chlorine, fluorine or bromine. The linear alkyl of 1 to 4 carbon atoms for $R_1$ and $R_4$ are preferably methyl, ethyl, n-propyl or n-butyl and the branched alkyl of 3 to 5 carbon atoms for $R_1$ are preferably isopropyl or isobutyl. Examples of $R_1$ as alkoxy of 1 to 4 carbon atoms are methoxy, ethoxy or n-propoxy.

Examples of acids for the preparation of non-toxic, pharmaceutically acceptable acid addition salts are inorganic acids such as hydrochloric acid, hydrobromic acid, sulfuric acid or phosphoric acid or sulfonic acids such as methane sulfonic acid or p-toluene sulfonic acid.

Among the preferred compounds of formula I are those wherein $R_1$ is in the 6,7, or 8-position, those wherein $R_2$ is hydrogen, those wherein $R_4$ is hydrogen, those wherein $R_4$ is methyl, those wherein $R_1$ is $-CF_3$, particularly in the 8-position, those wherein $R_1$ is branched alkyl of 3 to 5 carbon atoms particularly in the 6-position such as isopropyl, those wherein $R_1$ is hydrogen, those wherein $R_3$ is thiazolyl, those wherein $R_3$ is 4,5-dihydrothiazolyl and their non-toxic, pharmaceutically acceptable acid addition salts, and those wherein $R_3$ is imidazolyl and their non-toxic, pharmaceutically acceptable acid addition salts.

Particularly preferred are the compounds of formula I wherein $R_4$ is hydrogen, hydroxyl or alkyl of 1 to 4 carbon atoms and $R_3$ is thiazolyl and especially those where $R_1$ is $-CF_3$ in the 8-position, $R_2$ is hydrogen and $R_3$ is 2-thiazolyl.

Among specific compounds of formula I are N-(4,5-dihydro-2-thiazolyl)-4-hydroxy-8-trifluoromethyl-quinoline-3-carboxamide, N-(1H-imidazol-2-yl)-4-hydroxy-8-trifluoromethyl-quinoline-3-carboxamide and its non-toxic, pharmaceutically acceptable acid addition salts, N-(2-thiazolyl)-4-hydroxy-6-isopropyl-quinoline-3-carboxamide, N-(2-thiazolyl)-4-hydroxy-2-methyl-8-trifluoromethyl-quinoline-3-carboxamide, N-(2-thiazolyl)-4-hydroxy-quinoline-3-carboxamide, N-(2-thiazolyl)-4-hydroxy-2-ethyl-8-trifluoromethyl-quinoline-3-carboxamide, N-(2-thiazolyl)-4-hydroxy-2-isopropyl-8-trifluoromethyl-quinoline-3-carboxamide, N-(2-thiazolyl)-4-hydroxy-2-n-propyl-8-trifluoromethyl-quinoline-3-carboxamide, N-(2-thiazolyl)-4-hydroxy-2-n-butyl-8-trifluoromethyl-quinoline-3-carboxamide, N-(2-thiazolyl)-4-hydroxy-2-(2-methylpropyl)-8-trifluoromethyl-quinoline-3-carboxamide, N-(2-thiazolyl-2,4-dihydroxy-8-trifluoromethyl-quinoline-3-carboxamide, N-(2-thiazolyl)-4-hydroxy-2-benzyl-8-trifluoromethyl-quinoline-3-carboxamide, N-(2-thiazolyl)-4-hydroxy-2-phenyl-8-trifluoromethyl-quinoline-3-carboxamide, N-(2-thiazolyl)-4-hydroxy-6-trifluoromethyl-quinoline-3-carboxamide, N-(2-thiazolyl)-4-hydroxy-8-methoxy-quinoline-3-carboxamide and N-(2-thiazolyl)-4-hydroxy-6-chloro-quinoline-3-carboxamide.

The novel process of the invention for the preparation of compounds of formula I comprises reacting a compound of the formula

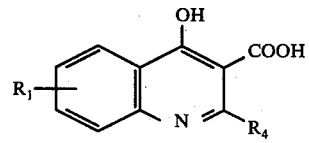

wherein $R_1$ and $R_4$ have the above definitions or a functional derivative thereof with an amine of the formula

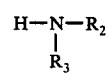

wherein $R_2$ and $R_3$ have the above definition.

Preferably, the functional derivative of the acid of formula II is the acid chloride or the ethyl ester. If the reaction is effected with the acid or acid chloride, the reaction is effected in the presence of pyridine. The reaction of the acid of formula II with the amine of formula III is preferably effected in the presence of dicyclohexylcarbodiimide in dimethylformamide.

The acid addition salts of the compounds of formula I where $R_3$ is imidazolyl or 4,5-dihydrothiazolyl may be prepared by reacting the appropriate compound of formula I with a approximately stoichiometric amount of the acid.

The acids of formula II or their functional derivatives are generally known and may be prepared, when they are not known, for example, by the process of French Pat. No. 7731M. By analogy with the process described in J. Med. Soc., Vol. 16 (8), 1973, p.875-9, a compound of the formula

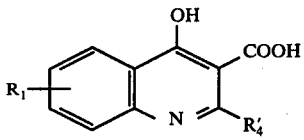

wherein $R_1$ has the above definition and $R_4'$ is alkyl of 1 to 4 carbon atoms, phenyl or benzyl may be prepared by reacting an aniline of the formula

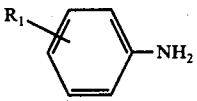

with an acyl chloride of the formula

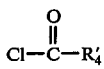

wherein $R_1$ and $R_4'$ have the above definitions to obtain a compound of the formula

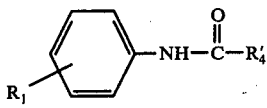

reacting the latter with phosphorus pentachloride to form a compound of the formula

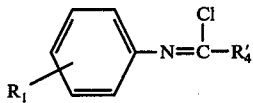

reacting the latter with ethoxy magnesium of ethyl malonate to obtain a compound of the formula

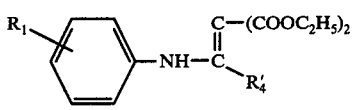

heating the latter to cyclize it to obtain a compound of the formula

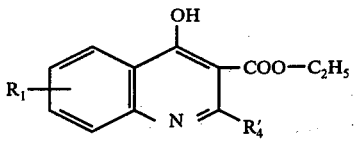

and saponifying the latter to obtain the compound of formula II'.

The compounds of formula II wherein $R_4$ is hydroxy, when they are not known, may be prepared by reaction of methyl $R_1$-2-aminobenzoate with malethyl chloride followed by cyclization to form the ethyl ester of the acid of formula II which is then saponified.

Novel intermediates of the invention are 4-hydroxy-6-isopropyl-quinoline-3-carboxylic acid and its acid chloride, 4-hydroxy-2-methyl-8-trifluoromethyl-quinoline-3-carboxylic acid and its acid chloride, 4-hydroxy-quinoline-3-carboxylic acid chloride, 4-hydroxy-2-ethyl-8-trifluoromethyl-quinoline-3-carboxylic acid and its ethyl ester, 4-hydroxy-2-isopropyl-8-trifluoromethyl-quinoline-3-carboxylic acid and its ethyl ester, 4-hydroxy-2-n-propyl-8-trifluoromethyl-quinoline-3-carboxylic acid and its ethyl ester, 4-hydroxy-2-n-butyl-8-trifluoromethyl-quinoline-3-carboxylic acid and its ethyl ester, 4-hydroxy-2-(2-methylpropyl)-8-trifluoromethyl-quinoline-3-carboxylic acid and its ethyl ester, ethyl 2,4-dihydroxy-8-trifluoromethyl-quinoline-3-carboxylate, 4-hydroxy-2-phenyl-8-trifluoromethyl-quinoline-3-carboxylic acid and its ethyl ester and 4-hydroxy-2-benzyl-8-trifluoromethyl-quinoline-3-carboxylic acid and its ethyl ester.

The novel analgesic compositions of the invention are comprised of an analgesically effective amount of at least one compound of formula I or its non-toxic, pharmaceutically acceptable acid addition salts when $R_3$ is 4,5-dihydrothiazolyl or imidazolyl and an inert pharmaceutical carrier. The compositions may be in the form of tablets, dragees, gelules, granules, suppositories, injectable solutions or suspensions, pomades, cremes, gels or aerosol preparations prepared by known methods.

Examples of suitable excipients are talc, starch, arabic gum, lactose, magnesium stearate, cacao butter, aqueous or non-aqueous vehicles, fatty bodies of animal or vegetable origin, paraffinic derivatives, glycols, preservatives, diverse wetting agents, dispersants or emulsifiers.

The compositions of the invention are useful for the treatment of muscular, articular or nervous pain, dental pain and migraines.

The novel method of the invention for relieving pain in warm-blooded animals, including humans, comprises administering to warm-blooded animals an analgesically effective amount of at least one compound of formula I or its non-toxic, pharmaceutically acceptable acid addition salts when $R_3$ is 4,5-dihydrothiazolyl or imidazolyl. The compounds may be administered orally, rectally, parenterally or topically by application to the skin or mucous. The dose varies depending upon the route of administration, the complaint treated and the person concerned. For example, the usual daily dose is 0.4 to 40 mg/kg by oral route.

In the following examples there are described several preferred embodiments to illustrate the invention. However, it should be understood that the invention is not intended to be limited to the specific embodiments.

EXAMPLE 1

N-(4,5-dihydro-2-thiazolyl)-4-hydroxy-8-trifluoromethyl-quinoline-3-carboxamide 6.3 g of 4-hydroxy-8-trifluoromethyl-quinoline-3-carboxylic acid chloride were added with stirring under an inert gas to 90 ml of pyridine and a solution of 2.35 g of 2-imino-2,3,4,5-tetrahydrothiazole in 15 ml of pyridine were added thereto. The mixture was stirred for 18 hours and was evaporated to dryness. The 11.5 g of residue were taken up in 40 ml of a 10% potassium carbonate solution and the solution was extracted with ethyl acetate. The combined organic phases were chromatographed over silica gel and the product was eluted with a 9-1 benzene-ethanol mixture. The elute was dried and the product was crystallized from ethanol to obtain 1.93 g of N-(4,5-dihydro-2-thiazolyl)-4-hydroxy-8-trifluoromethyl-quinoline-3-carboxamide melting at 267°–268° C.

EXAMPLE 2

N-(1H-imidazol-2-yl)-4-hydroxy-8-trifluoromethyl-quinoline-3-carboxamide hydrochloride

STEP A:
N-(1H-imidazol-2-yl)-4-hydroxy-8-trifluoromethyl-quinoline-3-carboxamide Using the procedure of Example 1, 11.57 g of 4-hydroxy-8-trifluoromethyl-quinoline-3-carboxylic acid chloride were reacted with 5.52 g of 2-aminoimidazole sulfate to obtain 3.9 g of N-(1H-imidazol-2-yl)-4-hydroxy-8-trifluoromethyl-quinoline-3-carboxamide melting at 211° C.

STEP B:
N-(1H-imidazol-2-yl)-4-hydroxy-8-trifluoromethyl-quinoline-3-carboxamide hydrochloride 10 ml of N hydrochloric acid were added to a suspension of 3.2 g of the product of Step A in 250 ml of water and the mixture was heated to 40°–50° C and filtered to remove insolubles. The aqueous filtrate was concentrated to 30 ml and was vacuum filtered. The recovered precipitate was washed with water and dried to obtain the dihydrate of N-(1H-imidazol-2-yl)-4-hydroxy-8-trifluoromethyl-quinoline-3-carboxamide hydrochloride.

Analysis: $C_{14}H_9F_3N_4O_2 \cdot HCl \cdot 2H_2O$. Calculated: %C 42.60, %H 3.57, %F 14.44, %N 14.19, %Cl 8.98. Found: %C 42.9, %H 3.4, %F 15.0, %N 14.1–14.3, %Cl 9.2.

EXAMPLE 3

N-(2-thiazolyl)-4-hydroxy-6-isopropyl-quinoline-3-carboxamide

STEP A: ethyl 4-(isopropylphenylaminomethylene)-propanedioate

A mixture of 33.80 g of 4-isopropylaniline and 54.06 g of ethyl ethoxymethylenemalonate was heated with stirring under an inert gas current to 130°–135° C while distilling ethanol and was then cooled to obtain 76.3 g of ethyl 4-(isopropylphenylaminomethylene)-propanedioate melting towards 35° C which was used as is for the next step.

STEP B: ethyl 4-hydroxy-6-isopropyl-quinoline-3-carboxylate

A mixture of 90 g of the product of Step A and 90 g of phenyl oxide was heated with stirring under an inert gas to 260°–270° C while distilling ethanol and the mixture was cooled and 30 ml of acetone were added thereto. The mixture was vacuum filtered and the precipitate was empasted with acetone and ether and was dried to obtain 34.5 g of ethyl 4-hydroxy-6-isopropyl-quinoline-3-carboxylate which sublimed at 269°–270° C and was used as is for the next step.

STEP C: 4-hydroxy-6-isopropyl-quinoline-3-carboxylic acid

A solution of 15 g of sodium hydroxide pastille in 150 ml of water was added under an inert gas to a stirred suspension of 34.5 g of the product of Step B in 150 ml of water and the mixture was refluxed to obtain an aqueous solution. The solution was washed with ether and acidified to a pH of 1 with concentrated hydrochloric acid. The mixture was vacuum filtered and the recovered product was washed with water and dried to obtain 29.6 g of product which was crystallized to obtain 22.87 g of 4-hydroxy-6-isopropyl-quinoline-3-carboxylic acid melting at 298° C which was used as is for the next step.

STEP D:
4-hydroxy-6-isopropyl-quinoline-3-carboxylic acid chloride 3.8 ml of thionyl chloride were added to a suspension of 10 g of the raw product of Step C in 300 ml of anhydrous benzene and the mixture was refluxed for 2½ hours and was then cooled. The mixture was vacuum filtered and the precipitate was empasted with a little anhydrous benzene to obtain 10.74 g of 4-hydroxy-6-isopropyl-quinoline-3-carboxylic acid chloride melting at 252° C.

STEP E:
N-(2-thiazolyl)-4-hydroxy-6-isopropyl-quinoline-3-carboxamide

Using the procedure of Example 1, 10.74 g of the product of Step D and 3.9 g of 2-amino-thiazole were reacted to obtain 1.28 g of N-(2-thiazolyl)-4-hydroxy-6-isopropyl-quinoline-3-carboxamide melting above 340° C.

Analysis: $C_{16}H_{15}N_3O_2S$; molecular weight = 313.381. Calculated: %C 61.32, %H 4.82, %N 13.41, %S 10.23. Found: %C 61.3, %H 4.7, %N 13.1, %S 10.1.

EXAMPLE 4

N-(2-thiazolyl)-4-hydroxy-2-methyl-8-trifluoromethyl-quinoline-3-carboxamide

STEP A: ethyl [1-(2-trifluoromethylphenylamino)-ethylidene]-propanedioate

A mixture of 48.4 g of diethylacetylmalonate and 38.7 g of trifluoromethylaniline was heated at 100° C for 1 hour and was then cooled and held at room temperature for 5 days. The solution was added to ether and the mixture was washed until the pH was 6. The mixture was dried, treated with activated carbon and dried to obtain an oil. The product was chromatographed over silica and was eluted with a 9-1 cyclohexane-ethyl acetate mixture to obtain 42.7 g of ethyl [1-(2-trifluoromethylphenylamino)-ethylidene]-propanedioate with an Rf = 0.12 which was used as is for the next step.

Analysis: $C_{16}H_{18}O_4F_3N$; molecular weight = 345.308. Calculated: %C 55.65, %H 5.24, %F 16.5, %N 4.05. Found: %C 55.7, %H 5.5, %F 14.6, %N 3.5.

STEP B: ethyl 4-hydroxy-2-methyl-8-trifluoromethyl-quinoline-3-carboxylate

A suspension of 5 g of the product of Step A and 10 g of phenyl oxide was heated to 240° C and was then cooled to room temperature. The phenyl oxide was evaporated and the resulting crystals were added to 20 ml of isopropyl ether. The mixture was filtered to obtain 2.9 g of ethyl 4-hydroxy-2-methyl-8-trifluoromethyl-quinoline-3-carboxylate melting at 165° C.

STEP C:
4-hydroxy-2-methyl-8-trifluoromethyl-quinoline-3-carboxylic acid

A suspension of 19.4 g of the product of Step B in 162 ml of N sodium hydroxide was refluxed for 5 hours and the mixture was then washed with ether and modified to a pH of 1 with N hydrochloric acid. The mixture was filtered and the solid precipitate was washed with water and dried to obtain 16.6 g of 4-hydroxy-2-methyl-8-trifluoromethyl-quinoline-3-carboxylic acid melting at 260° C.

STEP D: 4-hydroxy-2-methyl-8-trifluoromethyl-quinoline-3-carboxylic acid chloride Using the procedure of Step D of Example 3, the acid of Step C was reacted to form 4-hydroxy-2-methyl-8-trifluoromethyl-quinoline-3-carboxylic acid chloride.

STEP E: N-(2-thiazolyl)-4-hydroxy-2-methyl-8-trifluoromethyl-quinoline-3-carboxamide Using the procedure of Example 1, the product of Step D and 2-aminothiazole were reacted to obtain N-(2-thiazolyl)-4-hydroxy-2-methyl-8-trifluoromethyl-quinoline-3-carboxamide melting at 267° C.

EXAMPLE 5

N-(2-thiazolyl)-4-hydroxy-quinoline-3-carboxamide 3.8 ml of thionyl chloride were added to a suspension of 8.2 g of 4-hydroxy-quinoline-3-carboxylic acid in 160 ml of benzene and the mixture was refluxed for an hour and then cooled. The mixture was vacuum filtered and the precipiate was empasted with a little anhydrous benzene and was dried to obtain 9 g of 4-hydroxy-quinoline-3-carboxylic acid chloride melting at 260° C. The said product was then reacted with 4.35 g of 2-aminothiazole as in Example 1 to obtain 4.3 g of N-(2-thiazolyl)-4-hydroxy-quinoline-3-carboxamide melting at 349°–350° C.

EXAMPLE 6

N-(2-thiazolyl)-4-hydroxy-2-ethyl-8-trifluoromethyl-quinoline-3-carboxamide

STEP A: N-(2-trifluoromethylphenyl)-propanamide 33.3 g of propionyl chloride were added over 30 minutes at 20°–30° C to a mixture of 480 ml of acetone, 48.3 g of o-trifluoromethyl aniline and 36.42 g of triethylamine and after standing for 12 hours, the mixture was filtered. The acetone was evaporated from the filtrate and the residue was taken up in 500 ml of ethyl acetate. The solution was washed with 10% potassium carbonate solution, then with water until the pH of the wash waters was 6, then with N hydrochloric acid and then with water until the wash water pH was 6. The solution was dried over magnesium sulfate, treated with activated carbon and then evaporated to dryness to obtain 65 g of raw product which was washed with iced essence G to obtain 43 g of N-(2-trifluoromethylphenyl)-propanamide melting at 86° C.

STEP B: N-(2-trifluoromethylphenyl)-propanimidoyl chloride

A solution of 18 g of the product of Step A in 150 ml of toluene was added over 15 minutes to a suspension of 19 g of phosphorus pentachloride in 23 ml of toluene and after gas evolution ceased, the mixture was refluxed for 1½ hours. The toluene was evaporated under reduced pressure to obtain 19 g of N-(2-trifluoromethylphenyl)-propanimidoyl chloride in the form of a yellow oil which was used as is for the next step.

STEP C: ethyl 2-[1-(2-trifluoromethylphenylamino)-prop-1-ylidene]-propanedioate A mixture of 3.64 g of magnesium, 3.4 ml of absolute ethanol and 0.34 ml of carbon tetrachloride stood for a few minutes and then 88.5 ml of anhydrous ether were added thereto over 20 minutes. Then, a mixture of 24 g of ethyl malonate in 13.6 ml of absolute ethanol and 17 ml of anhydrous ether was added thereto over 15 minutes and reflux was naturally maintained for one hour. Ether was evaporated while replacing it with 40 ml of dry toluene and then 20 ml of toluene were added. Distillation of the toluene-ethanol azeotrope (b.p. — 76°–77° C with 68% ethanol) until pure toluene was distilled and the mixture was cooled and stood at room temperature to obtain ethoxy magnesium of ethyl malonate (Org. Syn. IV., p. 708) which was directly used.

A solution of 35.35 g of the product of Step B in 30 ml of dry toluene was added over 30 minutes at room temperature to the ethoxy magnesium of ethyl malonate and after standing at room temperature for 30 minutes, the mixture was poured into a mixture of 150 ml of ice and 15 ml of 2N hydrochloric acid. The mixture was extracted with ether and the ether extracts were washed with 5% sodium bicarbonate solution and with water until the wash water pH was 6. The ether phase was dried over magnesium sulfate, treated with activated carbon and was evaporated to obtain 53 g of ethyl 2-[1-(2-trifluoromethylphenylamino)-prop-1-ylidene]-propanedioate in the form of a yellow oil which was used as is for the next step.

STEP D: ethyl 4-hydroxy-2-ethyl-8-trifluoromethyl-quinoline-3-carboxylate

A suspension of 53 g of the product of Step C and 50 ml of phenyl oxide was heated for 20 minutes in a bath at 240° C and the resulting ethanol was distilled. The phenyl oxide was evaporated and the residue was taken up in 100 ml of isopropyl ether. The mixture was filtered and the filter was washed twice with 10 ml of isopropyl ether to obtain 19 g of ethyl 4-hydroxy-2-ethyl-8-trifluoromethyl-quinoline-3-carboxylate melting at 129° C which was used as is for the next step.

STEP E: 4-hydroxy-2-ethyl-8-trifluoromethyl-quinoline-3-carboxylic acid

A solution of 5 g of the product of Step D in 25 ml of 36° Bé sodium hydroxide solution and 50 ml of ethanol was refluxed for 3½ hours and was then cooled. The ethanol was evaporated and 100 ml of ice water were added thereto. The mixture was washed with methylene chloride and was acidified slowly by addition of 2N hydrochloric acid under 15° C. The mixture was filtered and the filtrate was washed with water until the wash water pH was 6 to obtain 4.4 g of 4-hydroxy-2-ethyl-8-trifluoromethyl-quinoline-3-carboxylic acid melting at 174° C which was used as is for the next step.

STEP F: N-(2-thiazolyl)-4-hydroxy-2-ethyl-8-trifluoromethyl-quinoline-3-carboxamide A mixture of 11 g of the product of Step E, 3.85 g of 2-aminothiazole, 7.94 g of dicyclohexylcarbodiimide and 110 ml of dimethylformamide was stirred under an inert gas for 72 hours and the mixture was filtered. The filtrate was evaporated to dryness and the residue was taken up in 100 ml of a 5% sodium bicarbonate solution. The mixture was filtered and was washed with water until the wash water pH was 6 to obtain 11.9 g of raw product. The latter was chromatographed over silica gel and was eluted with a 9–1 methylene chloride-ethyl acetate mixture to recover the fraction with an Rf = 0.18. The product was dried to obtain 7.6 g of product which was crystallized from acetic acid to obtain 6.5 g of N-(2-thiazolyl)-4-hydroxy-2-ethyl-8-trifluoromethyl-quinoline-3-carboxamide in the form of colorless crystals melting at 240° C.

Analysis: $C_{16}H_{12}N_3O_2SF_3$; molecular weight = 367.348. Calculated: %C 52.30, %H 3.30, %N 11.44, %S 8.72, %F 15.51. Found: %C 52.6, %H 3.5, %N 11.4, %S 9.0, %F 15.3.

EXAMPLE 7

4-hydroxy-2-isopropyl-N-(2-thiazolyl)-8-trifluoromethyl-quinoline-3-carboxamide

STEP A:
N-(2-trifluoromethylphenyl)-2-methyl-propanamide 34.5 g of isobutyl chloride were added over 15 minutes to a mixture of 46.7 g of o-trifluoromethylaniline, 32.6 g of triethylamine and 470 ml of acetone and the mixture was held at 15° C for 30 minutes and then returned to room temperature. The mixture stood for 12 hours and was filtered and the filtrate was evaporated to dryness. The residue was taken up in 700 ml of ethyl acetate and the solution was washed with 10% potassium carbonate solution and then with water until the wash water pH was 6, then with N hydrochloric acid and finally with water until the wash water pH was 6. The solution was dried over magnesium sulfate, was treated with activated carbon and was evaporated to obtain 68 g of raw product which was washed with hexane to obtain 60 g of N-(2-trifluoromethylphenyl)-2-methyl-propanamide melting at 114° C which was used as is for the next step.

STEP B:
N-(2-trifluoromethylphenyl)-2-methyl-propanimidoyl chloride

A solution of 11.56 g of the product of Step A in 200 ml of toluene was added over 15 minutes to a suspension of 11.45 g of phosphorus pentachloride in 25 ml of toluene and after gas evolution ceased, the mixture was refluxed for 1½ hours and was evaporated to dryness to obtain 12.4 g of N-(2-trifluoromethylphenyl)-2-methyl-propanimidoyl chloride as a yellow oil which was used as is for the next step.

STEP C: ethyl 2-[1-(2-trifluoromethylphenylamino)-2-methyl-prop-1-ylidene]-propanedioate Using the procedure of Step C of Example 6, 1.34 g of magnesium and 8.8g of ethyl malonate were reacted to obtain ethoxy magnesium of ethyl malonate to which was added over 30 minutes at room temperature a solution of 12.4 g of the product of Step B in 10 ml of dry toluene. The mixture was held at room temperature for 45 minutes and was then poured into 50 ml of 2N hydrochloric acid and 50 ml of ice. The mixture was extracted with ether and the extracts were washed with 5% sodium bicarbonate solution and then with water until the wash water pH was 6. The extracts were dried over magnesium sulfate, treated with activated carbon and evaporated to obtain 18 g of ethyl 2-[1-(2-trifluoromethylphenylamino)-2-methyl-prop-1-ylidene]-propanedioate in the form of a yellow oil which was used as is for the next step.

STEP D: ethyl 4-hydroxy-2-isopropyl-8-trifluoromethyl-quinoline-3-carboxylate A solution of 16 g of the product of Step C in 16ml of phenyl oxide was heated for 15 minutes on a bath at 240° C and the ethanol was distilled. The phenyl oxide was evaporated to obtain ethyl 4-hydroxy-2-isopropyl-8-trifluoromethylquinoline-3-carboxylate as a brown oil which was used as is for the next step.

STEP E:
4-hydroxy-2-isopropyl-8-trifluoromethyl-quinoline-3-carboxylic acid

A solution of 14 g of the product of Step D, 75 ml of 36° Bé sodium hydroxide and 150 ml of ethanol was refluxed for 6 hours and was then cooled. The ethanol was distilled and 150 ml of ice water were added. The mixture was washed with methylene chloride and was acidified with slow addition of 2N hydrochloric acid at less than 15° C. The mixture was filtered and washed until the wash waters had a pH of 6 to obtain 6.9 g of 4-hydroxy-2-isopropyl-8-trifluoromethyl-quinoline-3-carboxylic acid melting at 204° C which was used as is for the next step.

STEP F:
N-(2-thiazolyl)-4-hydroxy-2-isopropyl-8-trifluoromethyl-quinoline-3-carboxamide A mixture of 6.3 g of the product of Step E, 2.1 g of 2-aminothiazole, 4.74 g of dicyclohexylcarbodiimide and 130 ml of dimethylformamide was stirred for 72 hours and was then filtered. The filtrate was evaporated to dryness and the residue was taken up in 50 ml of a 5% sodium bicarbonate solution. The mixture was filtered and washed with water until the wash water were neutral to obtain 8 g of raw product. The latter was chromatographed and was eluted with a 9–1 methylene chloride-ethyl acetate to recover the fraction with an Rf = 0.25. The product was dried to obtain 6 g of product which was crystallized from acetone to obtain 4.2 g of N-(3-thiazolyl)-4-hydroxy-2-isopropyl-8-trifluoromethyl-quinoline-3-carboxamide in the form of colorless crystals melting at 213° C.

Analysis: $C_{17}H_{14}O_2N_3F_3S$; molecular weight = 381.368. Calculated: %C 53.53, %H 3.70, %N 11.02, %S 8.40, %F 14.94. Found: %C 53.6, %H 3.7, %N 10.9, %S 8.6, %F 15.1.

EXAMPLE 8

N-(2-thiazolyl)-4-hydroxy-2-n-propyl-8-trifluoromethyl-quinoline-3-carboxamide

STEP A: N-(2-trifluoromethylphenyl)-butanamide

Using the procedure of Step A of Example 6, 32.2 g of o-trifluoromethylaniline and 23.44 g of butyryl chloride were reacted to obtain 24.4 g of N-(2-trifluoromethylphenyl)-butanamide melting at 76° C which was used as is for the next step.

STEP B: N-(2-trifluoromethylphenyl)-butanimidoyl chloride

Using the procedure of Step B of Example 6, 23.1 g of the product of Step A and 22.9 g of phosphorus pentachloride were reacted to form 24.8 g of N-(2-trifluoromethylphenyl)-butanimidoyl chloride as an oil which was used as is for the next step.

STEP C: ethyl 2-[1-(2-trifluoromethylphenylamino)-but-1-ylidene]-propanedioate

Using the procedure of Step C of Example 6, 24.8 g of the product of Step C and ethoxy magnesium of ethyl malonate were reacted to form 37 g of ethyl 2-[1-(2-trifluoromethylphenylamino)-but-1-ylidene]-propanedioate as an oil which was used as is for the next step.

STEP D: ethyl 4-hydroxy-2-n-propyl-8-trifluoromethyl-quinoline-3-carboxylate

Using the procedure of Step D of Example 6, 37 g of the product of Step C were used to obtain 15.6 g of ethyl 4-hydroxy-2-n-propyl-8-trifluoromethyl-quinoline-3-carboxylate with a melting point of 98° C after crystallization from hexane which was used as is for the next step.

STEP E: 4-hydroxy-2-n-propyl-8-trifluoromethyl-quinoline-3-carboxylic acid

Using the procedure of Step E of Example 6, 13.5 g of the product of Step D were used to obtain 12.3 g of 4-hydroxy-2-n-propyl-8-trifluoromethyl-quinoline-3-carboxylic acid melting at 148° C after crystallization from isopropanol which was used as is for the next step.

STEP F: N-(2-thiazolyl)-4-hydroxy-2-n-propyl-8-trifluoromethyl-quinoline-3-carboxamide Using the procedure of Step F of Example 6, 6.3 g of the acid of Step E and 2.1 g of 2-amino-thiazole were reacted in the presence of dicyclohexylcarbodiimide in dimethylformamide to obtain 2.5 g of N-(2-thiazolyl)-4-hydroxy-2-n-propyl-8-trifluoromethyl-quinoline-3-carboxamide in the form of colorless crystals melting at 222° C after crystallization from acetic acid.

Analysis: $C_{17}H_{14}F_3N_3O_2S$; molecular weight = 381.36. Calculated: %C 53.53, %H 3.70, %N 11.02, %F 14.94, %S 8.40. Found: %C 53.6, %H 3.7, %N 11.0, %F 14.9, %S 8.5.

EXAMPLE 9

N-(2-thiazolyl)-4-hydroxy-2-butyl-8-trifluoromethyl-quinoline-3-carboxamide

STEP A: N-(2-trifluoromethylphenyl)-pentanamide

Using the procedure of Step A of Example 6, 32.22 g of o-trifluoromethyl aniline and 26.52 g of valeryl chloride were reacted to form 20.63 g of N-(2-trifluoromethylphenyl)-pentanamide melting at 63° C which was used as is for the next step.

STEP B: N-(2-trifluoromethylphenyl)-pentanimidoyl chloride

Using the procedure of Step B of Example 6, 20 g of the product of Step A and 19 g of phosphorus pentachloride were reacted to form 22.05 g of N-(2-trifluoromethylphenyl)-pentanimidoyl chloride as an oil which was used as is for the next step.

STEP C: ethyl 2-[1-(2-trifluoromethylphenylamino)-pent-1-ylidene]-propanedioate

Using the procedure of Step C of Example 6, 22.05 g of the product of Step C and ethoxy magnesium of ethyl malonate prepared from 14.62 g of ethyl malonate were reacted to obtain 31.68 g of ethyl 2-/1-(2-trifluoromethylphenylamino)-pent-1-ylidene/-propanedioate as an oil which was used as is for the next step.

STEP D: ethyl 4-hydroxy-2-butyl-8-trifluoromethyl-quinoline-3-carboxylate

Using the procedure of Step D of Example 6, 30.7g of the product of Step C were used to obtain 10g of ethyl 4-hydroxy-2-butyl-8-trifluoromethyl-quinoline-3-carboxylate melting at 68°–69° C which was used as is for the next step.

STEP E: 4-hydroxy-2-butyl-8-trifluoromethyl-quinoline-3-carboxylic acid

Using the procedure of Step E of Example 6, 9.9 g of the product of Step D were used to form 7.42 g of 4-hydroxy-2-butyl-8-trifluoromethyl-quinoline-3-carboxylic acid melting at 140°–141° C after crystallization from isopropanol which was used as is for the next step.

STEP F: N-(2-thiazolyl)-4-hydroxy-2-butyl-8-trifluoromethyl-quinoline-3-carboxamide Using the procedure of Step F of Example 6, 6.8 g of the product of Step E and 2.17 g of 2-aminothiazole were reacted in the presence of dicyclohexylcarbodiimide in dimethylformamide to form a raw product which was dissolved in aqueous N sodium hydroxide solution. Hydrochloric acid was added to the solution to obtain 4.15 g of N-(2thiazolyl)-4-hydroxy-2-butyl-8-trifluoromethyl-quinoline-3-carboxamide in the form of colorless crystals melting at 181° C after crystallization from isopropanol.

Analysis: $C_{18}H_{16}F_3N_3O_2S$; molecular weight = 395.407. Calculated: %C 54.68, %H 4.08, %F 14.41, %N 10.62, %S 8.11. Found: %C 54.8, %H 4.1, %F 14.5, %N 10.4, %S 8.3.

EXAMPLE 10

N-(2-thiazolyl)-4-hydroxy-2-(2-methylpropyl)-8-trifluoromethyl-quinoline-3-carboxamide STEP A: N-(2-trifluoromethylphenyl)-3-methyl-butanamide Using the procedure of Step A of Example 6, 40.28 g of o-trifluoromethyl aniline and 33.16 g of isovaleryl chloride were reacted to form 45.85 g of N-(2-trifluoromethyl)-3-methyl-butanamide melting at 99°–100° C which was used as is for the next step.

STEP B: N-(2-trifluoromethylphenyl)-3-methyl-butanimidoyl chloride

Using the procedure of Step B of Example 6, 45 g of the product of Step A and 42.02 g of phosphorus pentachloride were reacted to form 47.95 g of N-(2-trifluoromethylphenyl)-3-methyl-butanimidoyl chloride as an oil which was used as is for the next step.

STEP C: ethyl 2-[1-(2-trifluoromethylphenylamino)-3-methyl-but-1-ylidene]-propanedioate Using the procedure of Step C of Example 6, 47.95 g of the product of Step B and ethoxy magnesium of ethyl malonate prepared from 31.89g of ethyl malonate were reacted to form 72.45g of ethyl-2-[1-(2-trifluoromethylphenylamino)-3-methyl-but-1-ylidene]-propanedioate as an oil which was used as is for the next step.

STEP D: ethyl 4-hydroxy-2-(2-methylpropyl)-8-trifluoromethyl-quinoline-3-carboxylate Using the procedure of Step D of Example 6, 72.45 g of the product of Step C were used to obtain 44.7 g of ethyl 4-hydroxy-2-(2-methylpropyl)-8-trifluoromethyl-quinoline-3-carboxylate melting at 100° C which was used as is for the next step.

STEP E: 4-hydroxy-2-(2-methylpropyl)-8-trifluoromethyl-quinoline-3-carboxylic acid Using the procedure of Step E of Example 6, 20.14 g of the product of Step D were used to obtain 17.15 g of 4-hydroxy-2-(2-methylpropyl)-8-trifluoromethyl-quinoline-3-carboxylic acid melting at 200° C which was used as is for the next step.

STEP F: N-(2-thiazolyl)-4-hydroxy-2-(2-methylpropyl)-8-trifluoromethyl-quinoline-3-carboxamide Using the procedure of Step F of Example 6, 10.02 g of the product of Step E and 3.2 g of 2-aminothiazole were reacted in the presence of dicyclohexylcarbodiimide in dimethylformamide to obtain 4.03 g of N-(2-thiazolyl)-4-hydroxy-2-(2-methylpropyl)-8-trifluoromethyl-quinoline-3-carboxamide in the form of colorless crystals melting at 170°–171° C after crystallization from isopropanol.

EXAMPLE 11

N-(2-thiazolyl)-2,4-dihydroxy-8-trifluoromethyl-quinoline-3-carboxamide

STEP A: methyl 2-amino-3-trifluoromethyl-benzoate

Gaseous hydrochloric acid was bubbled through a refluxing mixture of 24.62 g of 2-amino-3-trifluoromethylbenzoic acid and 200 ml of anhydrous methanol for 22 hours and the mixture was then evaporated to dryness. The residue was taken up in ether and the solution was washed with water, then with a 10% potassium carbonate solution and then with water until the wash water was neutral. The ether solution was evaporated to dryness to obtain 20.64 g of methyl 2-amino-3-trifluoromethyl-benzoate in the form of an oil with a boiling point of 56°–58° C at 0.3 mm Hg which was used as is for the next step.

STEP B: methyl 2-(3-ethoxy-3-oxo-propanoylamino)-3-trifluoromethyl-benzoate A mixture of 24.4 g of the product of Step A and 18.36 g of malethyl chloride in 66 ml of anhydrous benzene was refluxed for an hour and was washed with water, then with a 10% potassium carbonate solution and then with water until the wash waters were neutral. The mixture was evaporated to dryness to obtain 35.75 g of methyl 2-(3-ethoxy-3-oxo-propanoylamino)-3-trifluoromethyl-benzoate melting at 87° C which was used as is for the next step.

STEP C: ethyl 2,4-dihydroxy-8-trifluoromethyl-quinoline-3-carboxylate 35.66 g of the product of Step B were added to 800 ml of anhydrous ether in the presence of sodium ethylate prepared from 2.69 g of sodium and 54 ml of ethanol and the mixture was vacuum filtered. The recovered precipitate was dissolved in water and the pH of the solution was adjusted to 1 by addition of 20% hydrochloric acid to obtain 30.56 g of ethyl 2,4-dihydroxy-8-trifluoromethyl-quinoline-3-carboxylate melting at 190° C which was used as is for the next step.

STEP D: N-(2-thiazolyl)-2,4-dihydroxy-8-trifluoromethyl-quinoline-3-carboxamide A mixture of 6.02 g of the product of Step C, 200 ml of xylene, 2 g of 2-amino-thiazole and 20 g of siliporite NK20 was refluxed for 2 hours and the resulting product was crystallized from acetic acid to obtain 5.54 g of N-(2-thiazolyl)-2,4-dihydroxy-8-trifluoromethyl-quinoline-3-carboxamide in the form of colorless crystals melting at 260° C.

Analysis: $C_{14}H_8F_3N_3O_3S$; molecular weight = 355.297. Calculated: %C 47.33, %H 2.27, %N 11.83, %F 16.04, %S 9.02. Found: %C 47.3, %H 2.2, %N 11.8, %F 16.2, %S 9.2.

EXAMPLE 12

N-(2-thiazolyl)-4-hydroxy-2-phenyl-8-trifluoromethyl-quinoline-3-carboxamide

STEP A: N-(2-trifluoromethylphenyl)-benzamide

Using the procedure of Step A of Example 6, 40.28 g of o-trifluoromethyl aniline and 35.14 g of benzoyl chloride were reacted in the presence of 25.3 g of triethylamine in 400 ml of acetone to obtain 41.45 g of N-(2-trifluoromethylphenyl)-benzamide melting at 146° C which was used as is for the next step.

STEP B: N-(2-trifluoromethylphenyl)-benzenecarboximidoyl chloride

Using the procedure of Step B of Example 6, 26.52 g of the product of Step A and 22.9 g of phosphorus pentachloride were reacted in 160 ml of dry toluene to obtain 28.8 g of N-(2-trifluoromethylphenyl)-benzenecarboximidoyl chloride as an oil which was used as is for the next step.

STEP C: ethyl 2-[phenyl-(2-trifluoromethylphenylamino)-methylene]-propanedioate Using the procedure of Step C of Example 6, 28.6 g of the product of Step B and ethoxy magnesium of ethyl malonate prepared from 2.68 g of magnesium and 17.6 g of ethyl malonate were reacted to form 32.6 g of ethyl 2-[phenyl-(2-trifluoromethylphenylamino)-methylene]-propanedioate melting at 84° C which was used as is for the next step.

STEP D: ethyl 4-hydroxy-2-phenyl-8-trifluoromethyl-quinoline-3-carboxylate

Using the procedure of Step D of Example 6, 31.56 g of the product of Step C and 32 ml of phenyl oxide were reacted to obtain 23.56 g of ethyl 4-hydroxy-2-phenyl-8-trifluoromethyl-quinoline-3-carboxylate melting at 114° C which was used as is for the next step.

STEP E: 4-hydroxy-2-phenyl-8-trifluoromethyl-quinoline-3-carboxylic acid

Using the procedure of Step E of Example 6, 12.64 g of the product of Step D in 35 ml of 36° Bé sodium hydroxide and 70 ml of 95% ethanol were refluxed for 5½ hours to obtain 9.06 g of 4-hydroxy-2-phenyl-8-trifluoromethyl-quinoline-3-carboxylic acid melting at 204° C which was used as is for the next step.

STEP F: N-(2-thiazolyl)-4-hydroxy-2-phenyl-8-trifluoromethyl-quinoline-3-carboxamide Using the procedure of Step F of Example 6, 8.9 g of the product of Step E and 2.70 g of 2-aminothiazole were reacted in the presence of 6.12 g of dicyclohexylcarbodiimide in 60 ml of dimethylformamide to obtain a raw product which was then dissolved in aqueous N sodium hydroxide. Hydrochloric acid was added thereto to obtain 4.42 g of N-(2-hiazolyl)-4-hydroxy-2-phenyl-8-trifluoromethyl-quinoline-3-carboxamide melting at 238° C after crystallization from acetic acid.

Analysis: $C_{20}H_{12}F_3N_3O_2S$; molecular weight = 415.397. Calculated: %C 57.83, %H 2.91, %N 10.11, %F 13.72, %S 7.72. Found: %C 58.0, %H 2.8, %N 10.0, %F 13.8, %S 8.0.

EXAMPLE 13

N-(2-thiazolyl)-4-hydroxy-2-phenylmethyl-8-trifluoromethyl-quinoline-3-carboxamide

STEP A: N-(2-trifluoromethylphenyl)-benzeneacetamide

Using the procedure of Step A of Example 6, 40.28 g of o-trifluoromethyl aniline and 42.5 g of phenylacetyl chloride were reacted in the presence of 27.83 g of triethylamine in 400 ml of benzene to obtain 29.85 g of N-(2-trifluoromethylphenyl)-benzeneacetamide melting at 104° C after crystallization from hexane which was used as is for the next step.

STEP B: N-(2-trifluoromethylphenyl)-benzeneethanimidoyl chloride

Using the procedure of Step B of Example 6, 27.92 g of the product of Step A and 22.9 g of phosphorus pentachloride in 170 ml of dry toluene were reacted to obtain 30.4 g of N-(2-trifluoromethylphenyl)-benzeneethanimidoyl chloride which was used as is for the next step.

STEP C: ethyl 2-[2-phenyl-1-(2-trifluoromethylphenylamino)-ethyl-1-ylidene]-propanedioate Using the procedure of Step C of Example 6, 30.4 g of the product of Step B and ethoxy magnesium of ethyl malonate (prepared from 2.68 g of magnesium and 17.6 g of ethyl malonate) were reacted to obtain 44.56 g of ethyl 2-[2-phenyl-1-(2-trifluoromethylphenylamino)-ethyl-1-ylidene]propanedioate which was used as is for the next step.

STEP D: ethyl 4-hydroxy-2-phenylmethyl-8-trifluoromethyl-quinoline-3-carboxylate Using the procedure of Step D of Example 6, 44.5 g of the product of Step C and 45 ml of phenyl oxide were reacted to obtain after chromatography 12.7 g of ethyl 4-hydroxy-2-phenylmethyl-8-trifluoromethyl-quinoline-3-carboxylate melting at 99° C after crystallization from ethanol which was used as is for the next step.

STEP E: 4-hydroxy-2-phenylmethyl-8-trifluoromethyl-quinoline-3-carboxylic acid Using the procedure of Step E of Example 6, a mixture of 9.4 g of the product of Step D, 25.2 ml of 36° Bé sodium hydroxide and 51 ml of 95% ethanol was refluxed for 6 hours to obtain 7.3 g of 4-hydroxy-2-phenylmethyl-8-trifluoromethyl-quinoline-3-carboxylic acid melting at 252° C which was used as is for the next step.

STEP F: N-(2-thiazolyl)-4-hydroxy-2-phenylmethyl-8-trifluoromethyl-quinoline-3-carboxamide Using the procedure of Step F of Example 6, 8.6 g of the product of Step E and 2.47 g of 2-amino-thiazole were reacted in the presence of 5.59 g of dicyclohexylcarbodiimide in 125 ml of dimethylformamide to obtain a raw product which was dissolved in aqueous N sodium hydroxide. Addition of hydrochloric acid yielded 2.76 g of N-(2-thiazolyl)-4-hydroxy-2-phenylmethyl-8-trifluoromethyl-quinoline-3-carboxamide in the form of slightly ocre colored crystals melting at 256° C.

Analysis: $C_{21}H_{14}F_3N_3O_2S$. Calculated: %C 58.74, %H 3.28, %F 13.27, %N 9.78, %S 7.46. Found: %C 58.6, %H 3.2, %F 13.4, %N 9.7, %S 7.6.

EXAMPLE 14

Tablets were prepared with 50 mg of N-(2-thiazolyl)-4-hydroxy-2-methyl-8-trifluoromethyl-quinoline-3-carboxamide, N-(2-thiazolyl)-4-hydroxy-2-ethyl-8-trifluoromethyl-quinoline-3-carboxamide, N-(2-thiazolyl)-4-hydroxy-2-isopropyl-8-trifluoromethyl-quinoline-3-carboxamide or N-(2-thiazolyl)-4-hydroxy-2-phenyl-8-trifluoromethyl-quinoline-3-carboxamide and sufficient excipient of lactose, starch, talc and magnesium stearate to obtain a final tablet of 350 mg.

PHARMACOLOGICAL DATA

Analgesic Activity

The test was based on that of Koster et al [Fed. Proc., Vol. 18 (1959), p-412] in which acetic acid intraperitoneally injected into mice provokes repeated twisting and stretching movements which persist more than 6 hours. Analgesics prevent or suppress this syndrom which is considered to be exteriorization of a diffuse abdominal pain. A 1% solution of acetic acid in water was used; the dose to cause this syndrom was, in there conditions, of 0.01 ml/g or 100 mg/kg of acetic acid. The test products were orally administered to the mice 30 minutes before the acetic acid injections and the mice were fasted for 24 hours before the test. The stretching were observed and counted for each mouse for 15 minutes starting right after the acetic acid injection and the results expressed as $AD_{50}$ or the dose which reduced by 50% the number of stretchings as compared to the control animals are reported in the following Table.

TABLE

| Product of Example | AD-mg/kg |
|---|---|
| 1 | 15 |
| 2 | 18 |
| 3 | 25 |
| 4 | 4 |
| 6 | 3 |
| 7 | 5 |
| 8 | 15 |

The results show that the products, particularly that of Example 6, possess an important analgesic activity.

Various modifications of the products and processes of the invention may be made without departing from the spirit or scope thereof and it should be understood that the invention is intended to be limited only as defined in the appended claims.

We claim:

1. A compound selected from the group consisting of the formula

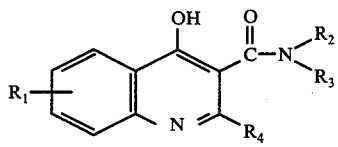

wherein $R_1$ is in the 5,6,7 or 8-position and is selected from the group consisting of hydrogen, halogen, —$CF_3$, —$OCF_3$, —$SCF_3$, straight chain alkyl of 1 to 4 carbon atoms, branched alkyl of 3 to 5 carbon atoms and alkoxy of 1 to 4 carbon atoms, $R_2$ is selected from the group consisting of hydrogen and methyl, $R_3$ is selected from the group consisting of 2-thiazolyl, 4,5-dihydrothiazolyl, pyridinyl, oxazolyl and 1H-imidazol-2-yl and $R_4$ is selected from the group consisting of hydrogen, hydroxyl, alkyl of 1 to 4 carbon atoms, phenyl and benzyl with the proviso that when $R_1$ is in the 7 or 8-position and is halogen, —$CF_3$, —$OCF_3$ or —$SCF_3$ and $R_4$ is hydrogen, $R_3$ is not thiazolyl, pyridinyl or oxazolyl and the non-toxic, pharmaceutically acceptable acid addition salts when $R_3$ is 1H-imidazol-2-yl or 4,5-dihydrothiazolyl.

2. A compound of claim 1 wherein $R_4$ is selected from the group consisting of hydrogen, hydroxyl and alkyl of 1 to 4 carbon atoms.

3. A compound of claim 2 wherein $R_1$ is in the 6,7 or 8-position.

4. A compound of claim 2 wherein $R_2$ is hydrogen.

5. A compound of claim 2 wherein $R_4$ is hydrogen.

6. A compound of claim 2 wherein $R_4$ is methyl.

7. A compound of claim 2 wherein $R_1$ is 8-$CF_3$.

8. A compound of claim 2 wherein $R_1$ is branched alkyl of 3 to 5 carbon atoms in the 6-position.

9. A compound of claim 8 wherein $R_1$ is isopropyl.

10. A compound of claim 2 wherein $R_1$ is hydrogen.

11. A compound of claim 2 wherein $R_3$ is 1H-imidazol-2-yl and its non-toxic, pharmaceutically acceptable acid addition salts.

12. A compound of claim 2 wherein $R_3$ is 4,5-dihydro-2-thiazolyl and its non-toxic, pharmaceutically acceptable acid addition salts.

13. A compound of claim 1 wherein $R_3$ is 2-thiazolyl.

14. A compound of claim 1 wherein $R_1$ is 8-$CF_3$, $R_2$ is hydrogen and $R_3$ is 2-thiazolyl.

15. A compound of claim 2 which is N-(2-thiazolyl)-4-hydroxy-2-methyl-8-trifluoromethyl-quinoline-3-carboxamide.

16. A compound of claim 2 which is N-(2-thiazolyl)-4-hydroxy-2-ethyl-8-trifluoromethyl-quinoline-3-carboxamide.

17. A compound of claim 2 which is N-(2-thiazolyl)-4-hydroxy-2-isopropyl-8-trifluoromethyl-quinoline-3-carboxamide.

18. An analgesic composition comprising an analgesically effective amount of at least one compound of claim 1 and an inert pharmaceutical carrier.

19. A composition of claim 18 wherein $R_4$ is selected from the group consisting of hydrogen, hydroxyl and alkyl of 1 to 4 carbon atoms.

20. A composition of claim 18 wherein $R_3$ is 2-thiazolyl.

21. A composition of claim 18 wherein the compound is selected from the group consisting of N-(2-thiazolyl)-4-hydroxy-2-methyl-8-trifluoromethyl-quinoline-3-carboxamide, N-(2-thiazolyl)-4-hydroxy-2-ethyl-8-trifluoromethyl-quinoline-3-carboxamide and N-(2-thiazolyl)-4-hydroxy-2-isopropyl-8-trifluoromethyl-quinoline-3-carboxamide.

22. A method of relieving pain in warm-blooded animals comprising administering to warm-blooded animals an analgesically effective amount of at least one compound of claim 1.

23. The method of claim 22 wherein $R_4$ is selected from the group consisting of hydrogen, hydroxyl and alkyl of 1 to 4 carbon atoms.

24. The method of claim 23 wherein $R_3$ is 2-thiazolyl.

25. The method of claim 23 wherein the compound is selected from the group consisting of N-(2-thiazolyl)-4-hydroxy-2-methyl-8-trifluoromethyl-quinoline-3-carboxamide, N-(2-thiazolyl)-4-hydroxy-2-ethyl-8-trifluoromethyl-quinoline-3-carboxamide and N-(2-thiazolyl)-4-hydroxy-2-isopropyl-8-trifluoromethyl-quinoline-3-carboxamide.

* * * * *

UNITED STATES PATENT OFFICE
CERTIFICATE OF CORRECTION

Patent No. 4,107,310            Dated Aug. 15, 1978

Inventor(s) Andre Allais, Francois Clemence, Roger Deraedt and Odile LeMartret

It is certified that error appears in the above-identified patent and that said Letters Patent are hereby corrected as shown below:

| Col. | Line | |
|---|---|---|
| [57] | | Abstract |
| | | "-CH$_3$" should be --CF$_3$-- |
| 10 | 46 | "N-(3" should be --N-(2-- |
| 17 | 39 | "4,5-dihydrothiazolyl" should be --4,5-dihydro-2-thiazolyl-- |
| 17 | 47 | " " " " " " " " " " " " " |

Signed and Sealed this

*First* Day of *January 1980*

[SEAL]

*Attest:*

SIDNEY A. DIAMOND

*Attesting Officer*      *Commissioner of Patents and Trademarks*